US00PP28360P3

(12) United States Plant Patent
Byrne et al.

(10) Patent No.: US PP28,360 P3
(45) Date of Patent: Sep. 5, 2017

(54) NECTARINE TREE NAMED 'SMOOTH TEXAN TWO'

(50) Latin Name: *Prunus persica*
Varietal Denomination: Smooth Texan Two

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 110 days.

(21) Appl. No.: 14/544,519

(22) Filed: Jan. 13, 2015

(65) Prior Publication Data

US 2016/0205829 P1 Jul. 14, 2016

(51) Int. Cl.
*A01H 5/08* (2006.01)

(52) U.S. Cl.
USPC ..... Plt./190

(58) Field of Classification Search
USPC ..... Plt./190
See application file for complete search history.

(56) References Cited

U.S. PATENT DOCUMENTS

PP12,620 P2 5/2002 Clark et al.

OTHER PUBLICATIONS

Philips. AgriLife Today, Dec. 30, 2013.*
The Brooks and Olmo Register of Fruit and Nut Varieties, 3rd Ed., American Society of Horticultural Science Press, Alexandria, VA, 1997.
Brooks, R. M. 1958. Double Delight, Earligold, and June Gold peaches. Fruit Var. J. 3:22.
Okie, W. R., R. W. Ramming, and R. Scorza. 1985. Peach, nectarine, and other stone fruit breeding by the USDA in the last two decades. HortScience 20: 633-641.

* cited by examiner

*Primary Examiner* — Keith Robinson
(74) *Attorney, Agent, or Firm* — Ramey & Schwaller, LLP

(57) ABSTRACT

Disclosed is a new variety of *Prunus persica* named 'Smooth Texan Two'. This new variety, which requires approximately 600 chilling units of dormancy, is considered to be a nectarine tree of early season maturity, which ripens in mid to late May in the medium chill zone of Texas and produces yellow fleshed fruit that are firm, attractively colored, and suitable for both local and regional markets.

5 Drawing Sheets

BACKGROUND OF THE INVENTION

Field of the Invention

This invention relates to nectarine trees and, more specifically, to nectarine trees referred to as a variety of *Prunus persica* named 'Smooth Texan Two'. 'Smooth Texan Two', which requires approximately 600 chilling units of dormancy, produces a high quality, firm yellow-fleshed clingstone nectarine that matures early in the season.

SUMMARY OF THE INVENTION

The 'Smooth Texan Two' nectarine is characterized as to novelty and is otherwise noteworthy by producing yellow-fleshed nectarine fruit that ripens in the early season; is considered high quality; and which has firm, yellow flesh and an attractive red skin coloration. In this regard, the present variety of nectarine tree bears fruit that are ripe for commercial harvesting and shipment about mid to late May, when the fruit is grown in the medium chill zone of Texas. 'Smooth Texan Two' ripens about 12 days before the 'June Gold' peach, a non-patented variety (Brooks, 1958). Additionally, the new variety exhibits the potential to be commercialized in regions that have chilling requirements that are relatively low.

ORIGIN OF THE VARIETY

The present nectarine tree was the result of an ongoing Stone Fruit Breeding Program of Texas A & M University, College Station, Brazos County, Tex. To this end, controlled crosses are made each year to produce seedling populations from which improved progenies are evaluated and selected.

The seedling 'Smooth Texan Two' originated at the Texas A & M University Horticultural Farm in College Station, Tex. in 2002. It was chosen from a population of seedlings that resulted from seed from a cross between female parent 'Crimson Baby' (not patented, Okie, 1998) and the male parent 'Bradley' (U.S. Plant Pat. No. 12,620). 'Bradley' is a non-melting, orange-yellow fleshed nectarine with high resistance to bacterial leaf spot [*Xanthamonas campestris* pv. pruni (Smith) Dye] from the Fruit Breeding Program of the University of Arkansas. It was selected among a F2 progeny from a hybrid between two unreleased Arkansas selections (A190 peach×A178 nectarine, both not patented) (Clark et al., 2002). 'Crimson Baby' is a cross between the University of Florida unreleased and not patented nectarine selection G69-83 [(Okinawa×Panamint)×Sunrise] and 'Mayfire' nectarine (not patented, Okie, 1998). 'Mayfire' is an early ripening yellow-fleshed nectarine released by the USDA Prunus breeding program in 1984 (Okie et al., 1985). Two-year and older trees of the variety were subsequently evaluated during the 2007 through 2011 fruit growing seasons in both California (Clovis) and Texas (College Station, Fairfield, and Terrell).

ASEXUAL REPRODUCTION OF THE VARIETY

'Smooth Texan Two' (TX3B195N) was bud grafted onto virus-free Nemaguard (not patented, Brooks and Olmo 1997) peach rootstock in June 2002 at the nursery site in Oakdale, Calif. The variety was subsequently planted at the experimental orchard in the central portion of the San Joaquin Valley, near Fowler, Fresno County, Calif. and in three sites in Texas (College Station, Fairfield, and Terrell). Fruit from the resulting propagation has been evaluated during the period from 2007 to 2011 fruit seasons. This evaluation clearly demonstrated that the re-propagated trees were true to the characteristics of the original seedling in all observable aspects.

BRIEF DESCRIPTION OF THE DRAWINGS

This new variety of nectarine tree is illustrated by the accompanying photographs. All fruit, flower, and shoots are from five-year old trees.

BOTANICAL DESCRIPTION OF THE VARIETY

Figure 1:
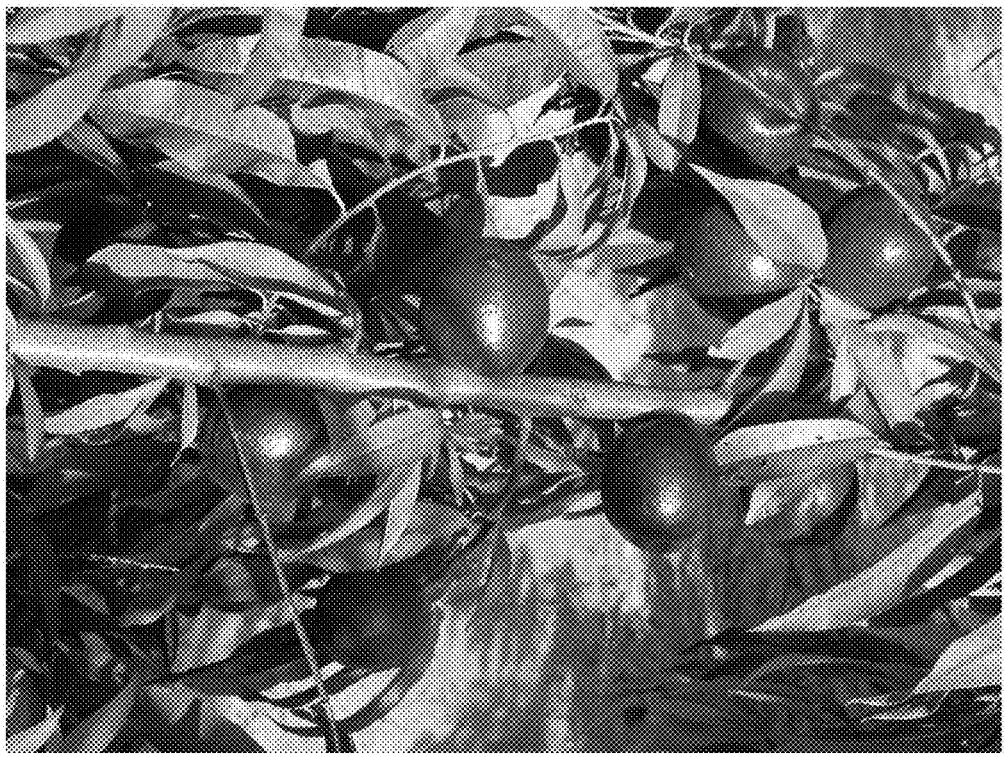
FIG. 1. A color photograph of a characteristic twig bearing typical leaves and several mature fruit showing their external coloration sufficiently matured for harvesting and shipment of 'Smooth Texan Two'. The shape of the fruit is slightly elongated because it was a low chill year.
Figure 2:
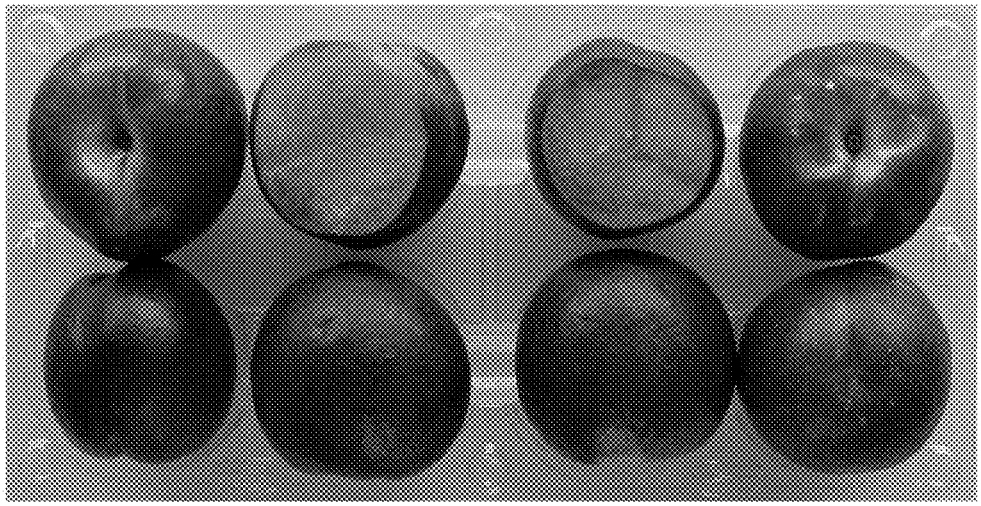
FIG. 2. Color picture showing the flesh and skin color and fruit shape of 'Smooth Texan Two' produced in the medium chill zone of Texas (Fairfield).
Figure 3:
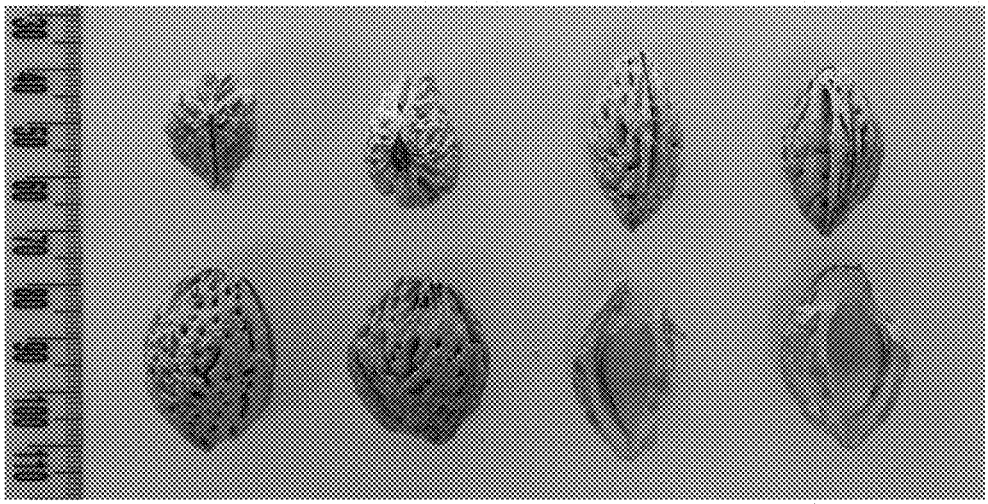
FIG. 3. Color photograph of the endocarp of 'Smooth Texan Two'. The ruler is demarcated in millimeters.
Figure 4:
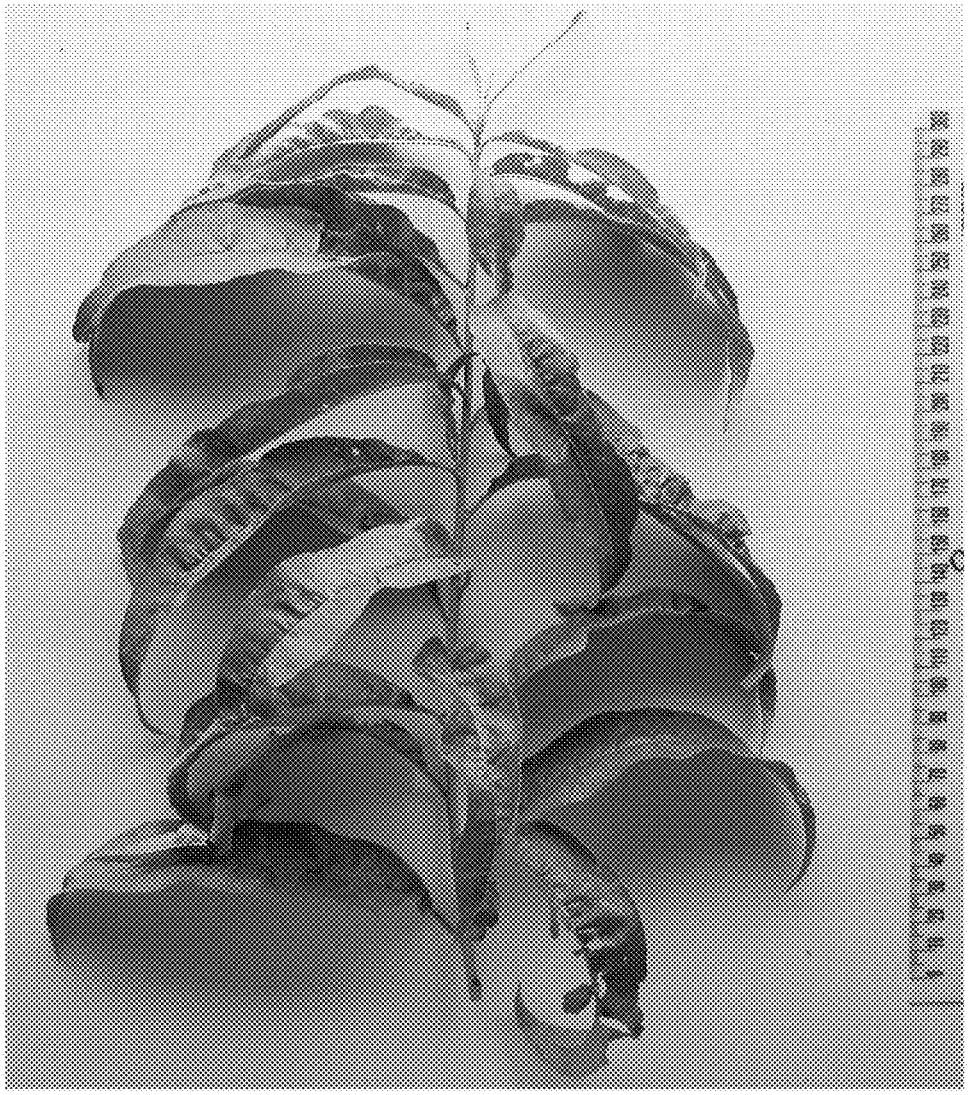
FIG. 4. A stem showing the leaves of the 'Smooth Texan Two' peach. The ruler is demarcated in millimeters.
Figure 5:
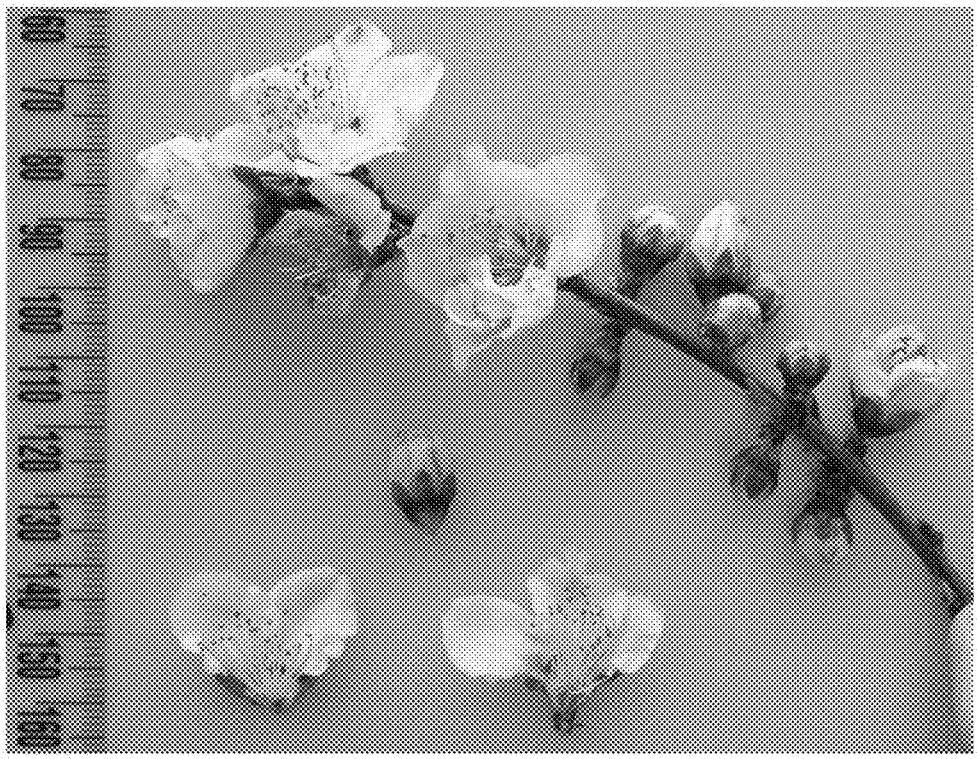
FIG. 5. The showy flowers of 'Smooth Texan Two'. The ruler is in millimeters.

Referring more specifically to the pomological details of this new and distinct variety of nectarine tree, the following has been observed under the ecological conditions prevailing at the experimental orchards in the medium chill zone of Texas. All major color code designations are by reference to The R.H.S. Colour Chart (2001) provided by The Royal Horticultural Society of Great Britain. Colors are approximate as color depends on horticultural practices such as light level and fertilization rate, among others. All observations were taken on five-year old trees.

Tree:

*Size*.—Generally average to above average as compared to other common nectarine cultivars ripening in the early season of maturity.

*Height*.—7 feet (2.13 m) at the end of the 2012 growing season on a five-year old tree.

*Width*.—4 feet (1.22 m) at the end of the 2012 growing season on a five-year old tree.

*Vigor*.—High.

*Density*.—Medium to high.

*Productivity*.—Productive.

*Shape*.—The trees are vigorous with the typical semi-spreading growth habit similar to 'TexKing' (U.S. Plant Pat. No. 14,627), 'TexPrince' (U.S. Plant Pat. No. 14,629), and 'TexRoyal' (not patented, Byrne and Bacon, 1991).

*Current season growth*.—The current season growth for the new variety was approximately 2.4 to 3.6 feet (0.73-1.1 m).

*Regularity of bearing*.—Regular, and considered hardy under typical conditions of the medium chill zone of Texas and the central San Joaquin Valley, Calif.

Trunk:

*Size*.—Approximately 3.5 inches (8.89 cm) in diameter and 11.5 inches (29.21 cm) in circumference when measured at a distance of approximately 12 inches (30.5 cm) above the soil level, at the end of the 2012 growing season on a five-year old tree.

*Bark texture*.—Considered moderately rough with numerous folds of papery scarf-like skin being present.

*Bark coloration*.—Variable, colors present are 166A of the Greyed-Orange Group, N200D Brown Group and 201D of the Brown Group.

Branches:

*Size*.—Considered medium to large for the variety.

*Thickness and length*.—Average (about 4.3 cm in diameter as measured 10 cm from the trunk on a five-year old tree) as compared to other varieties. The length of the branches are limited by pruning to a 3 to 5 foot (approximately 0.9 to 1.5 m) length depending on the position in the tree.

*Surface texture*.—Average and appearing furrowed on wood that is several years old.

*Lenticels*.—Numerous flat, oval lenticels present. The lenticels range in size from approximately 2 to 7 mm in width and were approximately 1 mm in height.

*Current season shoots*.—Surface texture — Substantially glabrous.

*Internode length*.—Approximately 2.1 to 2.4 cm as measured in the middle of a current season stem.

*Color of mature branches*.—The predominant colors are 166A of the Greyed-Orange Group, 187A and N187D of the Greyed-Purple Group and N200D of the Brown Group.

*Current season shoots*.—Color — Medium to light green (144A-B and N144D of Yellow-Green Group) with some reddish-brown coloration appearing on exposed surface of the shoots (165A-B, and 166C-D of the Greyed-Orange Group). The color of new shoot tips is considered a bright and shiny green (mainly Green Group 141A-C and 144A). The upper exposed surface of current season growth exhibit weak to medium intensity of anthocyanins.

Leaves:

*Size*.—Considered moderately large for the species. Leaf measurements have been taken from vigorous upright current season growth approximately at mid-shoot.

*Leaf length*.—Approximately 168 to 178 mm.

*Leaf width*.—Approximately 39 to 40 mm.

*Leaf thickness*.—Less than 1 mm.

*Leaf form*.—Lanceolate.

*Leaf tip form*.—Acuminate.

*Leaf upper surface color*.—Green approximately 137A-C of the Green Group.

*Leaf lower surface color*.—Green varying among 146A-B and 147B of the Yellow Green Group.

*Leaf mid-vein color.*—Light yellow green (1D of the Green-Yellow Group, 145C and 154D of the Yellow-Green Group).

*Leaf margins.*—

*Form.*—Considered crenate.

*Uniformity.*—Considered generally uniform.

*Leaf petioles.*—

*Size.*—Considered medium long.

*Length.*—Approximately 11 to 14 mm.

*Thickness.*—Approximately 2 mm.

*Color.*—Pale green (Yellow Green Group 145A and N144A-D).

*Leaf glands.*—

*Size.*—When present, approximately 2 mm in height and 1 mm in width.

*Number.*—Generally 0-2 per leaf.

*Type.*—Reniform.

*Color.*—Green with brown (Yellow-Green Group 144A and 199A, N199C-D of the Grey-Brown Group).

*Leaf stipules.*—

*Size.*—Medium-long for the species.

*Length.*—Approximately 10 to 13 mm.

*Width.*—Less than 1 mm at widest point.

*Form.*—Lanceolate.

*Color.*—Light green (144B-C of the Yellow-Green Group) with reddish brown tips (164B-C and 165C of the Greyed-Orange Group) when young. The stipules are considered to be early deciduous.

*Ratio of wood (leaf) buds to flowering buds.*—1 to 2 flower buds per vegetative bud.

Flowers:

*Floral buds.*—

*General.*—The floral buds are considered to be medium to medium large in size, conic in form, and slightly oppressed relative to the bearing shoot.

*Color.*—The bud scales are dark brown with orange, (approximately 177A of the Greyed-Orange Group and 200B-D of the Brown Group). The buds are considered hardy under typical conditions of the medium chill zone of Texas and the central San Joaquin Valley, Calif.

*Length.*—Approximately 5 to 6 mm.

*Width.*—Approximately 2.5-3.0 mm.

*Blooming type.*—Considered medium early in relation to other peach cultivars commonly growing in the medium chill zone of Texas. Date of full bloom was between March 1st and March 13th during the period between 2007 and 2011. Mean bloom date was March 7th which is about 2 days before 'June Gold' is in full bloom.

*Flower type.*—Showy.

*Flower size.*—Flower diameter at full bloom is approximately 33 to 42 mm. The length of the flower at the pink bud stage varies from 11 to 18 mm.

*Bloom quantity.*—Considered abundant.

*Flower bud frequency.*—Normally 1 to 2 per node.

*Petal size.*—

*General.*—Considered medium large for the species.

*Width.*—Approximately 15 to 18 mm.

*Length.*—Approximately 19 to 21 mm.

*Petal form.*—Broadly ovate.

*Petal count.*—Variable, from 5 to 16 per flower.

*Petal color.*—Light pink when young (Red-Purple Group 65C-D, 69A-B and Purple Group 75D), becoming lighter near the petal claw. Petal darkens with age (approximately Red-Purple N57D, 64D and 68B).

*Petal claw.*—

*Form.*—The claw is considered present.

*Length.*—Approximately 1 to 2 mm.

*Width.*—Approximately 1 mm.

*Petal margins.*—Generally considered variable, from nearly smooth to slightly undulate.

*Petal apex.*—Generally — The petal apices appear slightly domed.

*Flower pedicel.*—

*Length.*—Considered short, and having an average length of approximately 2 to 2.5 mm.

*Thickness.*—Considered average, approximately 0.5 to 1 mm.

*Color.*—A light green (Yellow-Green Group N144A-D).

*Floral nectaries.*—

*Color.*—Shiny orange (Orange Group N25A-B and Orange-Red Group 31A-B, 32B and 34A-B).

*Hypanthium.*—

*Surface texture.*—Generally glabrous.

*Color.*—A greenish brown (approximately Yellow-Green Group 146A-D and N144C and Greyed-Red Group 178A-C).

*Sepals.*—

*Surface texture.*—The surface has a short, fine, and wooly and a gray colored texture.

*Size.*—Average, and ovate in form. The sepals ranged from 4.5 to 5.2 mm in length and 3.4 to 4.1 mm in width when measured on flowers in the pink bud stage of development.

*Color.*—A dull red-purple with green (approximately Yellow-Green Group 144B-C, N144C and 146C-D and Greyed-Orange Group 176A-B).

*Anthers.*—

*General.*—Average in size for the species. The anthers are generally 1.0 mm in length and 0.5 mm in width.

*Color.*—Yellow (approximately Yellow Orange Group 18A and 20A-B).

*Pollen production.*—Pollen is abundant, and is a yellow color. Approximately Yellow Group 13A-B and Yellow-Orange Group 14C.

*Filaments.*—Size — Variable in length, approximately 16 to 19 mm, with the filaments slightly longer than the pistil. The stamens are generally above the pistil and do not protrude when the flower is at the pink bud stage of development.

*Color.*—White (approximately White Group N199D) developing a pink tinge (Red-Purple Group 62D and 65B-D) and darkening with advanced maturity (Red-Purple Group N66D, 71B-D and 72C-D).

*Pistil.*—

*General.*—Average in size, but slightly shorter, relative to the general anther height, overall.

*Length.*—Approximately 15 to 24 mm, including the ovary.

*Color.*—Considered a very light yellow-green when young (approximately Green-Yellow Group 1A-D), and becoming slightly darker with advancing senescence.

*Pubescence.*—Absent. The pistil including the ovary is not pubescent.

Fruit:

*Maturity when described*.—The present variety of fruit is described, as it would be found in its firm ripe condition at full commercial maturity. Under the ecological conditions prevailing in the medium chill zone of Texas 'Smooth Texan Two' ripens in mid to late May, a few days before 'Regal' (not patented, Okie, 1998) and about 10 days before 'June Gold'.

*Size*.—General — Medium to medium large for the season and considered uniform.

*Average cheek diameter*.—Approximately 62 to 71 mm.

*Average suture diameter*.—Approximately 61 to 79 mm.

*Average axial diameter*.—Approximately 65 to 77 mm.

*Fruit form*.—Generally round-ovate. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line.

*Color*.—The suture normally is the same color as the underlying blush (Greyed-Purple Group 183A-B and 185A).

*Ventral surface*.—Form — Considered uniform.

*Stem cavity*.—Size — Considered moderately shallow for the species.

*Width*.—Approximately 11 to 14 mm.

*Length*.—Approximately 12 to 15 mm.

*Depth*.—Approximately 9 to 10 mm.

*Form*.—Considered oval.

*Fruit base*.—Generally considered flat and uniform.

*Fruit apex*.—Generally considered flat and round.

*Fruit stem*.—Generally — Considered medium-long in length, approximately 9 to 11 mm. Thickness — Approximately 4 to 5 mm.

*Fruit skin*.—Generally considered medium or average in thickness. Surface Texture — Smooth. Skin Acidity — Considered neutral. Tenacious to Flesh — Yes at commercial maturity. Tendency to Crack — Not observed. Skin Color — Generally — Variable, with a small (40%) to a medium-(65%) percentage of the fruit surface covered with an attractive blush as described under Blush Color. Pubescence — Absent. The glabrous fruit has a medium glossiness. Blush Color — The blush color is generally more prevailing apically. This red blush ranges from red (Red Group 46A-B and Greyed-Purple Group 185A to 183A-B) to medium red (Greyed-Red Group 178A) with many degrees of shading and blending occurring between these colorations. The type of blush coloration would be categorized as a striped, chimeric or tigered covering. Skin Ground Color — This is generally present in variable percentages covering approximately 80-100% of the fruit's surface. The skin ground is a dark golden yellow color (Yellow Group 13A and Yellow-Orange Group 14A-B).

*Flesh color*.—Generally considered medium yellow (Yellow Group 13A-C and Yellow-Orange Group 14A-B).

*Flesh fibers*.—Present, numerous and lightly colored. These fibers are present throughout the flesh.

*Stone cavity color*.—Generally considered medium yellow (Yellow Group 11A-C).

*Flesh texture*.—Generally, the flesh is considered firm and fine at commercial maturity.

*Ripening*.—Generally the fruit of the present variety ripens evenly.

*Flavor*.—Considered sweet with an acidic flavor.

*Aroma*.—Pleasant and reasonably abundant.

*Eating*.—Generally considered very good, particularly for an early ripening variety.

Stone:

*Attachment*.—Clingstone (strongly adherent) at commercial maturity.

*Stone size*.—Generally considered medium relative to the ratio of stone to fruit size.

*Length*.—Approximately 31 to 32 mm.

*Width*.—Approximately 22 to 25 mm.

*Thickness*.—Approximately 16 to 17 mm

*Fibers*.—Generally a few medium length fibers are attached along the entire surface of the stone.

*Stone form*.—Generally the stone is considered elliptical.

*Stone base angle*.—Medium.

*Apex shape*.—The stone apex is wide.

*Stone shape*.—Considered elongated.

*Stone surface*.—

*Surface texture*.—Minor surface markings are honeycombed with numerous single pits and chains of pits.

*Ventral edge*.—Considered small to medium.

*Dorsal edge*.—Shape — Grooved and having moderately rough edges.

*Stone color*.—The color of the dry stone is light brown (159A of the Orange-White Group, 161D of the Greyed-Yellow Group and 164D and 165D of the Greyed-Orange Group). The color of the inside surface of the endocarp is primarily 158A-B of the Yellow-White Group, 159A-C of the Orange-White Group, 161D of the Greyed-Yellow Group and 164D and 165D of the Greyed-Orange Group.

*Tendency to split*.—Splitting is relatively uncommon.

*Kernel*.—The kernel fills the endocarp at harvest. When dried the shriveled kernels measure approximately 1 mm in thickness, 8 mm in width, and 16-18 mm in length. The colors of the shriveled kernels are primarily Greyed-Orange Group 164A and 165A-B and Greyed-Brown Group N199C-D.

*Use*.—The subject variety, 'Smooth Texan Two', is considered to be a nectarine tree of early-season maturity, which produces yellow-fleshed fruit which are firm, attractively colored, and which are useful for both local and long distance shipping.

*Keeping quality*.—Good to very good.

*Resistance to insects and disease*.—No particular susceptibilities were noted nor claimed.

*Shipping quality*.—Average. Although the new variety of peach tree possesses the described characteristics when grown under the ecological conditions prevailing in the medium chill zone of Texas, it will be understood that variations of the usual magnitude and characteristics incident to the changes in growing conditions, fertilization, pruning, and pest control are to be expected.

REFERENCES

Anon. 2001. R.H.S. Colour Chart. The Royal Hort. Soc., London.

Brooks, R. M. 1958. Double Delight, Earligold, and June Gold peaches. Fruit Var. J. 3:22.

Clark, J. R. and J. N. Moore. 2002. Nectarine tree named 'Bradley' cultivar. U.S. Plant Pat. No. 12,620, May 14, 2002.

Okie, W. R., R. W. Ramming, and R. Scorza. 1985. Peach, nectarine, and other stone fruit breeding by the USDA in the last two decades. HortScience 20: 633-641.

We claim:

1. A new and distinct *Prunus persica* tree, substantially as illustrated and described herein.

* * * * *